United States Patent [19]

Sunde

[11] Patent Number: 5,163,510
[45] Date of Patent: Nov. 17, 1992

[54] METHOD OF MICROBIAL ENHANCED OIL RECOVERY

[75] Inventor: Egil Sunde, Sandnes, Norway

[73] Assignee: Den norske stats oljeselskap a.s., Stavanger, Norway

[21] Appl. No.: 658,684

[22] Filed: Feb. 21, 1991

[30] Foreign Application Priority Data

Jan. 29, 1991 [GB] United Kingdom ............... 9101840

[51] Int. Cl.$^5$ ............................................. E21B 43/22
[52] U.S. Cl. ................................... 166/246; 166/268; 435/281
[58] Field of Search ................. 166/246, 268, 275; 252/8.554; 435/281

[56] References Cited

U.S. PATENT DOCUMENTS

| 2,742,398 | 4/1956 | ZoBell | 166/246 X |
| 2,807,570 | 9/1957 | Updegraff | 166/246 |
| 2,907,389 | 10/1959 | Hitzman | |
| 3,332,487 | 7/1967 | Jones | |
| 3,846,290 | 11/1974 | Raymond | 166/246 X |
| 4,349,633 | 9/1982 | Worne et al. | 435/281 |
| 4,401,569 | 8/1983 | Jhaveri et al. | 166/246 X |
| 4,475,590 | 10/1984 | Brown | 166/246 |
| 4,522,261 | 6/1985 | McInerney et al. | 166/246 |
| 4,588,506 | 5/1986 | Raymond et al. | 166/246 X |
| 4,678,033 | 7/1987 | Killough | 166/246 |
| 4,905,761 | 3/1990 | Bryant | 166/246 |
| 4,971,151 | 11/1990 | Sheehy | 166/246 |

FOREIGN PATENT DOCUMENTS

WO89/10463  11/1989  PCT Int'l Appl. .

Primary Examiner—George A. Suchfield
Attorney, Agent, or Firm—Foley & Lardner

[57] ABSTRACT

A method of microbial enhanced oil recovery for recovering oil from an oil-bearing rock formation. A population of aerobic bacteria is introduced into the formation at a position spaced from a production borehole. The micro-organisms are adapted to use oil as a carbon source. Pressurised injection water is introduced into the formation via an injection borehole, the water including a source of oxygen and mineral nutrients. The bacteria multiply using the oil as their main carbon source and the oxygen in the injection water as their main oxygen source. In so doing, they dissociate the oil from the rock formation and the dissociated oil is removed via the production borehole by the injection water.

36 Claims, 1 Drawing Sheet

METHOD OF MICROBIAL ENHANCED OIL RECOVERY

BACKGROUND TO THE INVENTION

The present invention relates to a method of microbial enhanced oil recovery.

When oil is present in subterranean rock formations such as sandstone or chalk, it can generally be exploited by drilling into the oil-bearing measures and allowing existing overpressures to force the oil up the borehole. This is known as primary removal. When the overpressure approaches depletion, it is customary to create an overpressure, for example by injecting water into the formations to flush out standing oil. This is known as secondary removal.

However, even after secondary removal, a great deal of oil remains in the formations; in the case of North Sea oil, this may represent 65% to 75% of the original oil present. Of this remaining oil probably more than half will be in the form of droplets and channels adhering to the rock formations that have been water-flooded and the remainder will be in pockets which are cut off from the outlets from the field. The present invention is concerned with the exploitation of the accessible but adhering oil remaining in the rock formations.

A number of enhanced oil recovery methods have been proposed, to address this objective. One approach is to combine pressure with a change in viscosity of the oil and/or water present. Thus, a diluent or $CO_2$ or steam is added to the reservoir to reduce the viscosity of the oil, thereby allowing it to be freed. Alternatively, viscosity-increasing additions such as polymers may be added to the injection water so that the oil is preferentially dislodged. However, the application of $CO_2$ is disadvantageous due to scale formation, the use of steam is only effective in shallow reservoirs of low temperature while the other additives are very costly.

Another approach is to alter the surface tension and capillary forces so that the water under pressure is more accessible to the pores and channels. This may be achieved by alkaline flooding or by means of surfactants. However, these approaches also tend to be costly.

Another approach is in situ combustion. This entails pumping air or oxygen into the formation and igniting the gas/oil present. In theory, the heat produced will mobilise the lighter fractions as a combustion front moves steadily through the formation, with the heavier tars burning. In practice, however, it is almost impossible to control the progress since the gases tend to rise while the water present sinks, resulting in an uneven combustion front.

A fourth approach is microbial enhanced oil recovery (MEOR). This entails the use of micro-organisms such as bacteria to dislodge the oil, and a number of systems have been proposed. In the case of unconsolidated measures, such as oil shales, the oil bearing rock may be pumped as an aqueous slurry to surface settling tanks or reservoirs where it is subjected to aerobic bacteria, as disclosed in U.S. Pat. No. 2907389. The availability of oxygen allows the bacteria to multiply, using the oil as a carbon source. In so doing, the bacteria produce surfactants which act to free the oil as droplets. The droplets of oil are less dense than water and so float to the surface. The oil is then removed. Unfortunately, the system cannot conveniently be applied to consolidated rock formations, particularly when they are undersea.

In situ MEOR methods generally fall into two categories, aerobic bacteria systems, as described typically in U.S. Pat. No. 3332487 and anaerobic bacteria systems as described in WO 89/10463.

The very existence of oil in a formation means that there cannot be present any anaerobic bacteria which will feed on oil under the prevailing conditions. Thus, in anaerobic bacteria systems, a source of carbon or "food" must be supplied. However, the bacteria selected (either deliberately or naturally) will be those most suited under the prevailing conditions to the consumption of the particular food employed. They will not be specifically adapted to have an effect on oil and therefore their action on oil will be as it were a by-product. Anaerobic systems therefore tend to be very slow in achieving the desired liberation of oil.

The absence of any oxygen in oil bearing formations means that if an aerobic system is to be used, then oxygen must be supplied. However, when aerobic bacteria are used and oxygen (or air, containing oxygen) is injected into the formation, the situation is far from satisfactory. Firstly, there is an immediate separation into a gaseous and an aqueous phase, which makes control of the system very difficult and in practice, limits the system to a batch-type operation. Secondly, a great deal of heat is generated, which, in view of the oxygen-rich gaseous phase and the readily available combustible material, presents a considerable risk of explosion. A cooling medium must therefore also be employed.

SUMMARY OF THE INVENTION

It is therefore an object of the present invention to provide a method of MEOR which enables residual oil to be recovered more rapidly than is possible with anaerobic systems but without the risk of explosion.

It is a further object of the invention to provide such a method which can be readily controlled and which will be continuous, that is to say, after initiation in a particular zone, the process will proceed until substantially all the oil is recovered, without the need to retreat the zone.

According to the invention, there is provided a method of microbial enhanced oil recovery for recovering oil from an oil-bearing second rock formation, the formation including an inlet at a first location and an outlet at a second location, the method comprising: injecting water containing a source of oxygen, capable of yielding at least 5 mg/l free oxygen, into the formation at the first location spaced apart from the second location, allowing micro-organisms, which are either already present in the formation or which are introduced simultaneously with the oxygen containing injection water to multiply using the oil as their main carbon source and the oxygen from the injection water as their main oxygen source thereby establishing a biomass layer which acts to dissociate the oil from the rock formation, the dissociated oil then being removed via the outlet by the injection water.

In this system, on the far side of the injection well, the oxygen becomes the growth limiting factor due to the consumption of oxygen by the micro-organisms. The rate of growth of micro-organisms is of course dependent on the available oxygen. In general maximum growth is desired and therefore it is desirable to maintain a high oxygen concentration in the injection water (and clearly also in advancing biomass layer). In some situations, where for instance it is desirable to stimulate the production of surfactants, level of oxygen and any nutrients in the water phase might be reduced, or intermittently reduced, in order to stress the micro-organisms into producing surfactants. This is at least one useful purpose in being able to adjust the oxygen concentration in the injection water.

A situation can then be established in which the biomass layer forms a front between the oxygen-rich injection water and oxygen-depleted water on the outlet side of the front. Initially, the oxygen-depleted water will be the formation water or oxygen free injection water but as the process progresses, it will be displaced by injection water, stripped of its oxygen as it passes through the biomass layer. Where the biomass is in contact with oil and has access to oxygen, it will feed on the oil, thereby dissociating the oil from the rock by one or more of a number of mechanisms. The principal mechanism is believed to be the production of surfactants which reduce the forces attaching the oil to the rock. The pressure of the injection water then forces the oil out of the rock pores and the oil is carried forwards by the injection water.

The oxygen is all consumed by the biomass, thus maintaining the front as the injection water passes through. Any oil degrading micro-organisms that are washed out by the water will become dormant due to the lack of oxygen. As the displaced oil is washed forwards, the micro-organisms at the rear of the front will have no oil and will either become dormant or will feed on each other. This effectively regulates the thickness of the biomass layer ensuring that the oxygen penetrates to the forward part of the layer, allowing fresh oil to be acted upon. Thus, the front advances through the oil towards the outlet and dislodged oil is constantly being flushed out by the injection water.

By a process of natural selection, only the most successful micro-organisms thrive and these will be the ones most effective in using the oil. They will therefore be the most efficient at dislodging the oil, probably by the production of surfactants. However, due to the flushing action of the injection water, the displaced oil is removed and so only a very small proportion of the oil will actually be consumed by the biomass.

One theory as to how the oil is dissociated is that the oil is split into small droplets by the surfactants and these are washed out. However, the present applicants believe that the oil is initially disposed in long strands or ribbons in the rock pore structure and that the surfactants begin to effect only portions of these strands. In this way, the overall viscous forces attaching a strand will be reduced and the injection water pressure eventually dislodges the entire strand, rather than its being broken up by the surfactants.

The micro-organisms may be any convenient single-cell organisms such as yeasts but are most preferably bacteria. Suitable bacteria may be *Pseudomonas putida*, *Pseudomonas aeruginosa*, *Corynebacterium lepus*, *Mycobacerium rhodochrous*, *Mycobacterium vaccae*, *Acinetobacter* and *Nocardia*. The bacteria used may be pre-selected and cultivated to thrive in the injection water under the prevailing conditions.

The oxygen in the injection water is preferably present as dissolved gas, though conceivably, it may be present as some other known oxidising agent either in solution or suspension. Suitable oxidising agents might be $H_2O_2$, $NaClO_3$, $KClO_4$, $NaNO_3$. Since the pressures involved with the injection water are necessarily very high to enable the water to be injected, the amount of gaseous oxygen that can be dissolved is quite considerable. The pressures encountered in the oil-bearing formations may be from 200 to 800 bar (20–80 MPa); at these pressures up to 4.0 g of oxygen may be dissolved in a liter of water. This quantity is amply sufficient to allow aerobic bacteria to multiply at a satisfactory rate with a bulk flow rate of the injection water which is low enough to avoid reservoir damage.

Preferably, therefore, the amount of oxygen dissolved will be from 1 mg/l to 4000 mg/l more preferably from 40 mg/l to 400 mg/l though the actual amount will be dependent upon the prevailing conditions. The amount of oxygen present should not be so much as would be toxic to the bacteria.

The micro-organisms will in all probability produce $CO_2$ as they multiply. However when dissolved oxygen in the injection water is used, the volume of $CO_2$ produced will be in a 1:1 molar ratio with the oxygen consumed and will therefore enter into solution, particularly since its solubility is much higher than that of oxygen. More $CO_2$ than indicated by this ratio may be produced by other reactions, in which oxygen is taken from other sources, e.g. water, once the bio degradation of hydro-carbon molecules has been initiated. Even where an oxidising agent is used, the solubility of $CO_2$ will be sufficient to avoid phase separation. The $CO_2$ produced will have a beneficial effect on the recovery of oil from the formation.

In practice, the avoidance of a gas phase is very important since microbial activity can only proceed in the liquid phase. Clearly, if a gas phase is present, the oil adhering to the rock formation within the gas phase will remain unaffected by the micro-organisms.

While many nutrient requirements of the micro-organisms may be met by the minerals naturally present, the injection water may have added to it essential nutrients, in particular to provide a source of nitrogen and phosphates. Examples of nutrient additives include $NaNO_3$, $KNO_3$, $NH_4NO_3$, $Na_2HPO_4$, $K_2HPO_4$, $NH_4Cl$.

It will be appreciated that by using a system according to the invention, the advancing biomass layer will remove effectively all the oil it encounters. Either the oil will be dislodged and flushed away or it will be consumed and converted since any oil not dislodged will remain in the oxygen-rich side. Thus, a single continuous operation should be sufficient to treat a particular zone. The liberated oil can be separated from the water, minerals and organic material by conventional methods though it is desirable to minimise any pre-separation exposure to air in order to avoid further microbial action on the oil.

When the formation is depleted there is no need for further operations of the kind indicated—the production zone will be shut down.

DESCRIPTION OF THE PREFERRED EMBODIMENT

The invention will also be illustrated with reference to a laboratory scale, controlled test procedure carried out by Terje Torsvik, Roald Nilsen and Janiche Beeder, all of the Dept. of Microbiology and Plant Physiology, University of Bergen.

Figure 1:
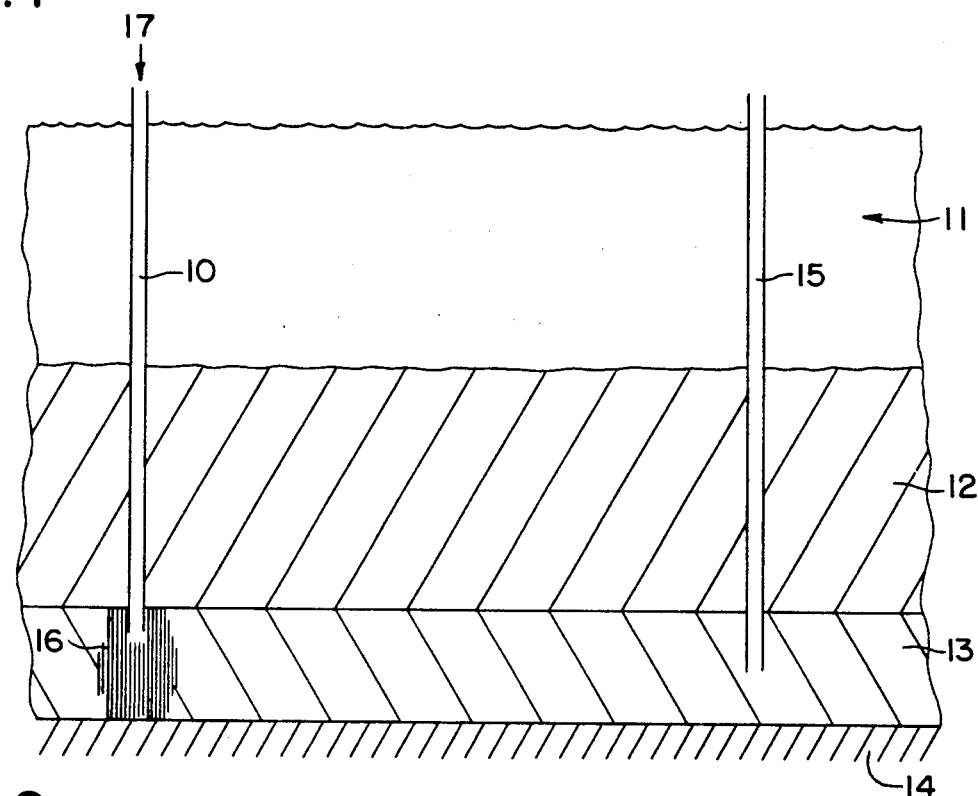
FIG. 1 is a schematic vertical section showing the initiation of a method according to the invention in a residual oil-bearing formation.

FIG. 1 shows an undersea oil well which has been subjected to primary/secondary removal by means of an injection well 10. Beneath the sea 11 there are various core strata 12, a residual oil bearing formation 13 and an underlying bed rock 14. A producing borehole 15 and the injection borehole 10 extend into the formation 13. In the case of a North Sea oilfield such as the Gullfaks field, the formation 13 might be consolidated sandstone which has a large quantity of adhering oil and which is flooded with formation and injection water containing no oxygen.

Injection water 17 is introduced into the formation 13 via the injection well 10. If there are no aerobic bacteria present in the formation 13 either naturally or due to operations carried out previously aerobic bacteria will be introduced via the injection well 10 e.g. with the injection water 17. The injection water 17 is rich in oxygen and various mineral nutrients such as ammonia and phosphates.

When the oxygen-rich injection water 17, the bacteria and the oil come into mutual contact, the bacteria attacks the oil, and multiplies, creating biofilm 16 converting some of the oil to lighter fractions and producing surface active agents or surfactants. The production well 15 will act as a sink and there will be an overall flow of bioorganic matter (biofilm) produced by the micro-organisms, oil and injection/formation water from the injection well 10 towards the production well 15.

The injection water 17 is moving through the formation 13 towards the borehole 15 at a speed of about 0.1-15 m/day carrying the formation/injection water before it. The formation water is removed via the borehole 15. The surfactants produced by the biofilm 16 help to reduce the forces by which the oil is attached to the rock formation and so the flowing injection water 17 actually detaches the oil 18 and this is carried forward through the formation 15.

As the injection water 17 passes through the biofilm 16, the oxygen is consumed by the multiplying bacteria. A steady state is reached when the thickness of the bacteria layer is such that no oxygen escapes the forward end. At this stage, the bacteria at the forward end of the layer receive less oxygen than the bacteria at the rear and so multiply more slowly. However, the bacteria at the rear run out of food (oil) and so they die. This tends to reduce the thickness of the layer and so more oxygen reaches the forward layers enabling the bacteria there to multiply. In this way, the bacteria layer moves steadily through the formation 13 at a rate of about 0.1 to 15 m/day. The oxygen is thus the controlling factor of the bacterial action. Any oil-degrading bacteria which is washed out by the injection water will cease to be active once it has left the bacteria layer since there will be no available oxygen.

Figure 3:
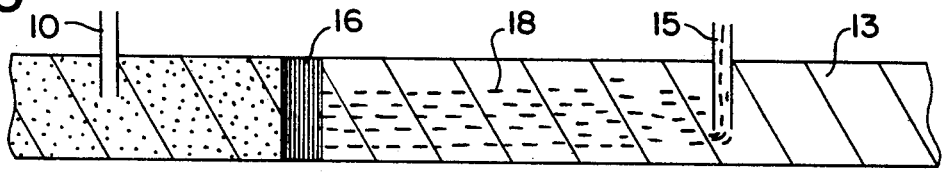

As shown in FIG. 3, the detached oil 18 flows out into the borehole 15 with the injection water. This is recovered at the surface and separation is carried out in a known manner.

Figure 4:
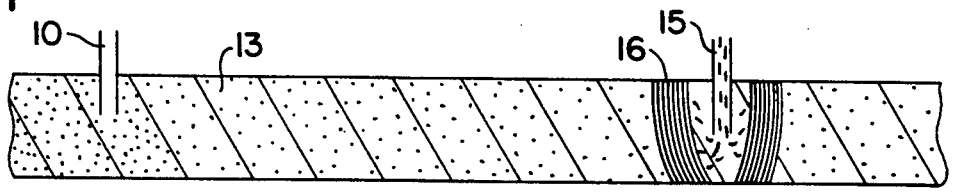

Eventually, the biofilm 16 reaches the borehole 15 and the well is shut down as shown in FIG. 4. The formation 13 will then be depleted of the oil previously adhering there.

Figure 2:
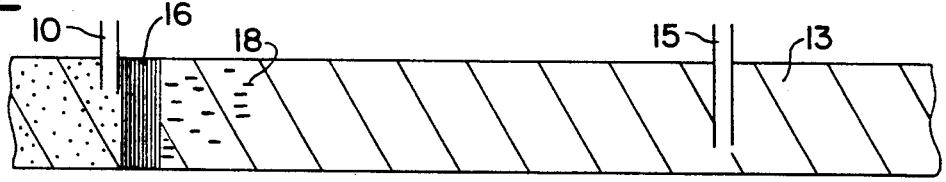
FIGS. 2 to 4 are similar simplified views showing sequential steps in the process.

While FIGS. 1 to 3 show the effect of the invention in one dimension, it will be appreciated that in practice, the situation would be a good deal more complex. In particular, the bacteria 16 would be arranged to converge on the borehole 15 from many or all directions, as depicted schematically in FIG. 4. Furthermore, there would probably be a number of boreholes, which would be in use simultaneously.

The described method is not in any way was restricted to teritary oil recovery. It can be used simultaneously to the injection of water in secondary oil recovery, as well as at the start of production of and oil field if an when the injection of water is found feasible. As will be evident to those skilled in the art, the use of water injection optionally in combination with this method will depend on the chosen strategy for producing hydrocarbons from a certain oil field.

TEST EXAMPLE I

A Hopeman sandstone core measuring 5×45 cm containing residual oil after water flooding was used. The core had the following specification:

| Volume | 884 cm$^3$ |
| --- | --- |
| Pore Volume | 166 cm$^3$ |
| Permeability | 700 mD |
| Residual oil | 61 cm$^3$ |
| Wettability | water wet |

Injection water, including bacterial inocula comprising a mixed population of aerobic oil degraders grown at 45° C., was passed through the core at a nominal pressure of 2 bar and at a superficial velocity of 0.5 m per day. The temperature was maintained at 45° C. The composition of the injection water was as follows:

| $K_2HPO_4$ | 1.0 g/l |
| --- | --- |
| $NH_4Cl$ | 0.25 g/l |
| NaCl | 20.0 g/l |
| $MgCl_2 \cdot 6H_2O$ | 3.0 g/l |
| KCl | 0.5 g/l |
| $CaCl_2 \cdot 2H_2O$ | 0.15 g/l |
| $NaHCO_3$ | 1.8 g/l |
| 5 ml/l vitamin solution | |
| 1 ml/l trace element solution | |
| Oxygen 1 mg/l | |

Under these conditions, an additional 5.5 cm$^3$ of oil were produced during the passing of 22 pore volume equivalents. This gives a ratio of 2.5 cm$^3$ oil produced for each mg of oxygen injected which is an oxygen efficiency of 2500.

Obviously, numerous modifications and variations of the present invention are possible in the light of the above teachings. It is therefore to be understood that within the scope of the appended claims, the invention may be practised otherwise than as specifically described herein.

I claim:

1. A method of microbial enhanced oil recovery for recovering oil from an oil-bearing rock formation, there being a source of micro-organisms present in said formation, said formation including an inlet at a first location and an outlet at a second location, said method comprising:
    injecting injection water containing a source of oxygen, capable of yielding at least 5 mg/l free oxygen, into said formation at said first location spaced apart from said second location;

allowing said micro-organisms, which are present in said formation to multiply using said oil as their main carbon source and said oxygen from said injection water as their main oxygen source, whereby a biomass layer is established which acts to dissociate said oil from said rock formation; and removing the dissociated oil removed via said outlet by said injection water.

2. A method according to claim 1 wherein said micro-organisms are bacteria.

3. A method according to claim 2 wherein said bacteria substantially comprises oil degrading aerobic and facultative anaerobic bacteria.

4. A method according to claim 3 wherein said bacteria substantially comprises species of a genus selected from the group consisting of *Pseudomonas putida, Pseudomonas aeruginosa, Corynebacterium lepus, Mycobacterium rhodochrous* and *Mycobacterium vaccae*.

5. A method according to claim 3 wherein said bacteria substantially comprises species selected from the group consisting of Acinetobacter and Nocardia.

6. A method according to claim 1 wherein said source of oxygen in said injection water is dissolved gaseous oxygen.

7. A method according to claim 1 wherein said source of oxygen in said injection water is provided by an oxidising compound selected from the group consisting $H_2O_2$, $NaClO_3$, $KClO_4$, $NaNO_3$ and combinations thereof.

8. A method according to claim 7 wherein said oxidising compound is used in combination with dissolved gaseous oxygen.

9. A method according to claim 1 wherein the concentration of said oxygen in said formation water is between about 1 mg/l and about 4000 mg/l.

10. A method according to claim 9 wherein said oxygen concentration is below a level which is toxic to said micro-organisms.

11. A method according to claim 1 wherein said injection water also includes mineral nutrients.

12. A method according to claim 11 wherein said mineral nutrients include a source of nitrogen and a source of phosphates.

13. A method according to claim wherein the superficial velocity of said injection water through said oil-bearing formation is between about 0.1 and 15 m/day.

14. A method according to claim 1 wherein said micro-organisms produce surfactants which act to dislodge the oil.

15. A method according to claim 14 wherein said supply of oxygen and any nutrients in said injection water is intermittently substantially reduced in order to induce the production of surfactants by said microorganism.

16. A method according to claim 15 wherein the reduction is carried out for periods of 5 to 50 hours.

17. A method according to claim 1 applied to a plurality of inlets or outlets from said oil-bearing formation.

18. A method according to claim 1 wherein said inlets and outlets are boreholes.

19. A method of microbial enhanced oil recovery for recovering oil from an oil-bearing rock formation, said formation including an inlet at a first location and an outlet at a second location, said method comprising:

injecting injection water containing a source of oxygen capable of yielding at least 5 mg/l free oxygen, and further containing a source of micro-organisms into said formation at said first location spaced apart from said second location;

allowing said micro-organisms which are introduced simultaneously with said oxygen containing injection water, to multiply using said oil as their main carbon source and said oxygen from said injection water as their main oxygen source, whereby a biomass layer is established which acts to dissociate said oil from said rock formation; and removing the dissociated oil via said outlet by said injection water.

20. A method according to claim 19 wherein said micro-organisms are bacteria.

21. A method according to claim 20 wherein said bacteria substantially comprises oil degrading aerobic and facultative anaerobic bacteria.

22. A method according to claim 21 wherein said bacteria substantially comprises species of a genus selected from the group consisting of *Pseudomonas putida, Pseudomonas aeruginosa, Corynebacterium lepus, Mycobacterium rhodochrous* and *Mycobacterium vaccae*.

23. A method according to claim 21 wherein said bacteria substantially comprises species selected from the group consisting of Acinetobacter and Nocardia.

24. A method according to claim 19 wherein said source of oxygen in said injection water is dissolved gaseous oxygen.

25. A method according to claim 19 wherein said source of oxygen in said injection water is provided by an oxidising compound selected from the group consisting of $H_2O_2$, $NaClO_3$, $KClO_4$, $NaNO_3$ and combinations thereof.

26. A method according to claim 25 wherein said oxidising compound is used in combination with dissolved gaseous oxygen.

27. A method according to claim 19 wherein the concentration of said oxygen in said formation water is between about 1 mg/l and about 4000 mg/l.

28. A method according to claim 19 wherein said oxygen concentration is below a level which is toxic to said micro-organisms.

29. A method according to claim 19 wherein said injection water also includes mineral nutrients.

30. A method according to claim 29 wherein mineral nutrients include a source of nitrogen and a source of phosphates.

31. A method according to claim 19 wherein the superficial velocity of said injection water through said oil-bearing formation is between about 0.1 and 15 m/day.

32. A method according to claim 19 wherein said micro-organisms produce surfactants which act to dislodge the oil.

33. A method according to claim 32 wherein said supply of oxygen and any nutrients in said injection water is intermittently substantially reduced in order to induce the production of surfactants by said micro-organisms.

34. A method according to claim 33 wherein the reduction is carried out for periods of 5 to 50 hours.

35. A method according to claim 19 applied to a plurality of inlets or outlets from said oil-bearing formation.

36. A method according to claim 19 wherein said inlets and outlets are boreholes.

* * * * *